United States Patent

Heeres et al.

[11] Patent Number: 5,571,811
[45] Date of Patent: Nov. 5, 1996

[54] SULFONAMIDE DERIVATIVES OF AZOLONES

[75] Inventors: Jan Heeres, Vosselaar; Raymond A. Stokbroekx, Beerse; Joseph H. Mostmans, Antwerpen; Louis J. E. Van der Veken, Vosselaar, all of Belgium

[73] Assignee: Janssen Pharmaceutica N.V., Beerse, Belgium

[21] Appl. No.: 447,505

[22] Filed: May 23, 1995

[30] Foreign Application Priority Data

Jul. 12, 1994 [EP] European Pat. Off. .............. 94202015

[51] Int. Cl.$^6$ ...................... A61K 31/495; C07D 403/02; C07D 403/14
[52] U.S. Cl. ........................ 514/252; 544/236; 544/257; 544/364; 544/366; 544/295; 544/370
[58] Field of Search .......................... 514/252; 544/370, 544/365, 364, 295, 236, 257

[56] References Cited

U.S. PATENT DOCUMENTS

| | | | |
|---|---|---|---|
| 4,791,111 | 12/1988 | Heeres et al. | 514/252 |
| 4,931,444 | 6/1990 | Van Wauwe et al. | 514/252 |
| 5,254,553 | 10/1993 | Heeres et al. | 514/252 |

*Primary Examiner*—Mukund J. Shah
*Assistant Examiner*—Richard S. Myers, Jr.
*Attorney, Agent, or Firm*—Charles J. Metz

[57] ABSTRACT

The invention is concerned with the compounds having the formula (I)

$$R^6-S(O)_2-N(piperazine)-N-(A)-N-C(=O)-N(R^1)-C(R^2)(R^3)-Z-Ar(R^4,R^5), \quad Y$$

the pharmaceutically acceptable addition salts and the stereochemically isomeric forms thereof, wherein Y is CH or N; $R^1$, $R^2$ and $R^3$ each independently are hydrogen or $C_{1-4}$alkyl; $R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy; $R^6$ is $C_{1-4}$alkyl; or phenyl optionally substituted with halo, $C_{1-4}$alkylcarbonylamino, $C_{1-4}$alkyloxy, $C_{1-4}$alkyl or nitro; Z is C=O or CHOH; and

—(A)— is a radical of formula (a-1), (a-2), (a-3), (a-4), (a-5), (a-6) or (a-7)

Compositions comprising said compounds, processes for preparing the same and the use of these compounds as a method of treating Helicobacter infection.

16 Claims, No Drawings

SULFONAMIDE DERIVATIVES OF AZOLONES

The present invention is concerned with substituted azolone derivatives which are potent anti-Helicobacter agents.

U.S. Pat. No. 4,791,111 discloses azolones having a structure similar to that of the present compounds and which are intermediates in the preparation of [[4-[4-(4-phenyl-1-piperazinyl)phenoxymethyl]-1,3-dioxolan-2-yl]methyl]-1H-imidazoles and -1H-1,2,4-triazoles.

In U.S. Pat. No. 4,931,444 are described substituted azolone derivatives having 5-lipoxygenase inhibiting activity. The present compounds are distinguished therefrom by their useful anti-Helicobacter activity.

In the eradication of Helicobacter, dual therapies comprising the separate administration of two antibiotic drugs have not been satisfactory because of one or more of the following reasons: a low eradication rate, numerous side effects and development of resistance by Helicobacter. Triple therapies comprising the administration of two antibiotics and a bismuth compound have been shown to be effective, but are very demanding for the patients and are also compromised by side effects. The present compounds show the avantage that they may be used in a monotherapy in the eradication of Helicobacter pylori and related species. The present invention is concerned with compounds having the formula

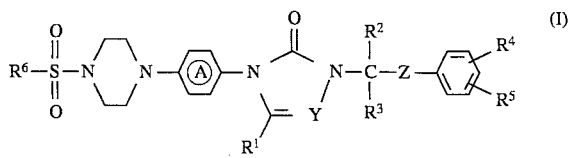

the pharmaceutically acceptable addition salts and the stereochemically isomeric forms thereof, wherein Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is $C_{1-4}$alkyl; or phenyl optionally substituted with halo, $C_{1-4}$alkylcarbonylamino, $C_{1-4}$alkyloxy, $C_{1-4}$alkyl or nitro;

Z is C=O or CHOH; and

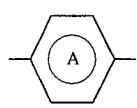

is a radical of formula

 (a-1)

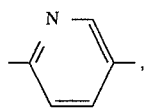 (a-2)

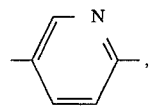 (a-3)

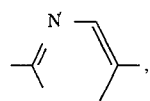 (a-4)

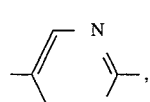 (a-5)

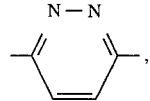 (a-6)

or

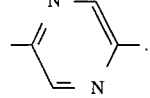 (a-7)

As used in the foregoing definitions halo defines fluoro, chloro, bromo and iodo; $C_{1-4}$alkyl defines straight and branched chain saturated hydrocarbon radicals having from 1 to 4 carbon atoms: methyl, ethyl, propyl, 1-methylethyl, butyl, 1-methylpropyl, 2-methylpropyl and 1,1-dimethylethyl. $C_{1-6}$alkyl defines $C_{1-4}$alkyl radicals as defined hereinbefore and the higher homologs thereof having from 5 to 6 carbon atoms such as, for example, pentyl and hexyl.

The term pharmaceutically acceptable addition salt as used hereinbefore defines the nontoxic, therapeutically active addition salt forms which the compounds of formula (I) may form. The compounds of formula (I) having basic properties may be convened into the corresponding therapeutically active, non-toxic acid addition salt forms by treating the free base form with a suitable amount of an appropriate acid following conventional procedures. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention. The absolute configuration of each chiral center may be indicated by the stereochemical descriptors R and S. For the compounds having two chiral centers, the relative stereodescriptors R* and S* are used in accordance with the Chemical Abstracts rules (Chemical Substance Name Selection Manual (Calif.), 1982 Edition, Vol. III, Chapter 20).

Some compounds of the present invention may exist in different tautomeric forms and all such tautomeric forms are intended to be included within the scope of the present invention.

A first group of interesting compounds are those compounds of formula (I) wherein $R^4$ is halo and $R^5$ is hydrogen.

A second group of interesting compounds are those compounds of formula (I) wherein

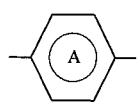

is a radical of formula (a–1) or (a–2).

A third group of interesting compounds are those compounds of formula (I) wherein Y is N and $R^1$ is hydrogen.

A fourth group of interesting compounds are those compounds of formula (I) wherein $R^2$ is $C_{1-4}$alkyl and $R^3$ is hydrogen.

A fifth group of interesting compounds are those compounds of formula (I) wherein $R^6$ is $C_{1-4}$alkyl.

Preferred compounds are those compounds of formula (I) wherein $R^1$, $R^3$ and $R^5$ are hydrogen; $R^2$ is $C_{1-4}$alkyl; $R^4$ is halo; and Y is N.

More preferred compounds are those compounds of formula (I) wherein $R^1$, $R^3$ and $R^5$ are hydrogen; $R^2$ is ethyl; $R^4$ is halo; Y is N; $R^6$ is $C_{1-4}$alkyl; and

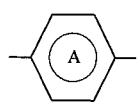

is a radical of formula (a–1) or (a–2).

The most preferred compound is 1-[5-[2-[1-[(4-chlorophenyl)hydroxymethyl]propyl]-2,3-dihydro-3-oxo-4H-1,2,4-triazol-4-yl]-2-pyridinyl]-4-(methylsulfonyl)piperazine, the pharmaceutically acceptable addition salts and the stereochemically isomeric forms thereof. Analogous procedures for the preparation of compounds such as the present compounds of formula (I) have been described in U.S. Pat. No. 4,791,111 and U.S. Pat. No. 4,931,444.

In particular, the compounds of formula (I) can be prepared by the reaction of an intermediate of formula (II) with a reagent of formula (III), in a reaction-inert solvent, e.g. dichloromethane, N,N-dimethylformamide and the like, optionally in the presence of a base, e.g. triethylamine.

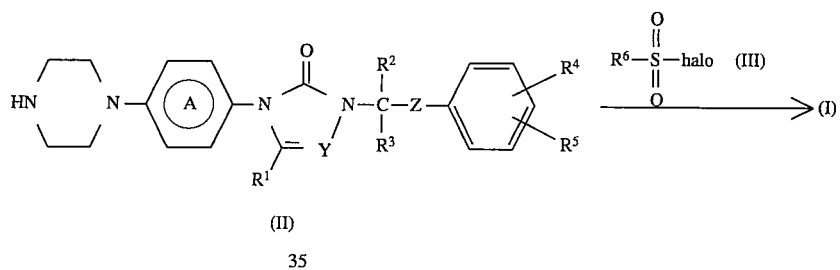

Alternatively, the compounds of formula (I) can be prepared by N-alkylating an intermediate of formula (V) with a reagent of formula (VI) in an appropriate solvent and in the presence of a suitable base.

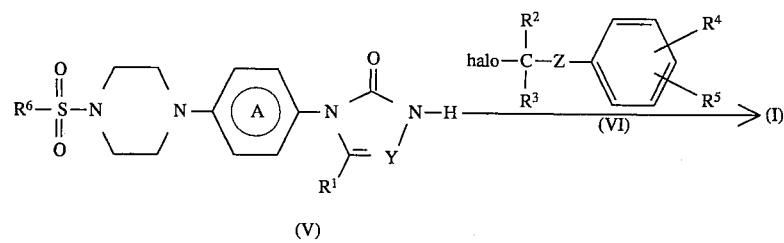

The compounds of formula (I) can also be converted into each other following art-known procedures of functional group transformation.

For example, the compounds of formula (I) wherein Z represents C=O can be converted into the compounds of formula (I) wherein Z represents CHOH following art-known reductions. For example, said reduction can conveniently be conducted by reaction with a metal hydride or complex metal hydride, e.g. sodium borohydride, sodium cyanoboro-hydride and the like in water, 1-methyl-pyrrolidinone, acetonitrile, an alcoholic medium, e.g. methanol, ethanol, or an ether, e.g. tetrahydrofuran, 1,4-dioxane; or in a mixture of such solvents.

Alternatively, said reduction can be conducted by reaction with tris(1-methylethoxy)-potassium hydroborate, tris(1-methylpropyl)sodium hydroborate or tris(1-methyl-propy- 1)potassium hydroborate in a reaction-inert solvent, e.g. tetrahydrofuran or N,N-dimethylformamide.

Optionally, the reaction of the intermediate of formula (II) with the reagent of formula (III) and the reduction reaction described above may be conducted in a single reaction vessel.

Finally, pure isomeric forms of the compounds of formula (I) can be separated from the mixture by conventional separation methods. In particular, the enantiomers may be separated by column chromatography using a chiral stationary phase such as a suitably derivatized cellulose, for example, tri(dimethylcarbamoyl)cellulose (Chiralcel OD®) and similar chiral stationary phases.

In all foregoing and in the following preparations, the reaction products may be isolated from the reaction mixture and, if necesarry, further purified according to methodologies generally known in the art.

The intermediates of formula (II) may be prepared by the reaction of a compound of formula (IV) with an acid, e.g. hydrobromic acid and the like.

animals, particularly humans, suffering from Helicobacter related diseases or afflictions. Examples of said diseases or afflictions are gastritis, stomach ulcers, duodenal ulcers and gastric cancer.

In view of their useful anti-Helicobacter properties, the subject compounds may be formulated into various pharmaceutical forms for administration purposes. To prepare the pharmaceutical compositions of this invention, an effective amount of the particular compound, in base or addition salt form, as the active ingredient is combined in intimate admixture with a pharmaceutically acceptable carder, which may take a wide variety of forms depending on the form of preparation desired for administration. These pharmaceutical compositions are desirably in unitary dosage form suitable, preferably, for administration orally, rectally, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solu-

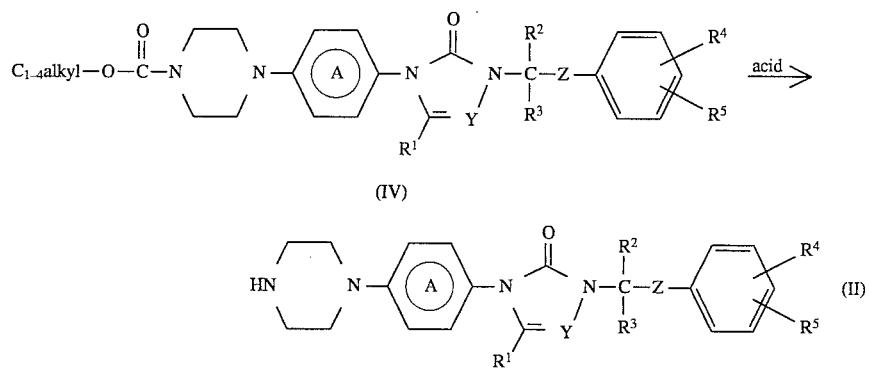

The intermediates of formula (V) may be prepared following the procedures as described hereinabove for the preparation of the compounds of formula (I) from the intermediates of formula (II).

The compounds of formula (I), the pharmaceutically acceptable addition salts and the stereochemically isomeric forms thereof display useful pharmacological activity against Helicobacter species; e.g. *Helicobacter pylori, Helicobacter mustelae, Helicobacter felis* and the like, in particular *Helicobacter pylori*.

Particularly important in this context is the finding that the subject compounds show inhibitory activity against the growth of Helicobacter as well as bactericidal activity against said bacteria. The bactericidal effect on Helicobacter was determined with suspension cultures by means of a procedure described in Antimicrob. Agents Chemother., 1991, vol. 35, pp. 869–872.

An interesting feature of the present compounds relates to their highly specific activity against Helicobacter. The compounds of formula (I) were found to show no inhibitory activity against any of the following species: *Campylobactor jejuni, Campylobacter coli, Campylobacter fetus, Campylobacter sputorum, Vibrio spp., Staphylococcus aureus* and *Escherichia coli*, tested at concentrations up to $10^{-5}$ M.

An important asset of the present compounds is their sustained activity against *H. pylori* at pH below the neutral pH. Activity at a low pH in vitro may indicate that a compound is not adversely affected by the acidic environment of the stomach in vivo.

Consequently, the subject compounds are considered to be valuable therapeutical drugs for treating warm-blooded tions: or solid carders such as starches, sugars, kaolin, lubricants, binders, disintegrating agents and the like in the case of powders, pills, capsules and tablets. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

When the pharmaceutical composition takes the form of an aqueous solution, those compounds of formula (I) which display low solubility may be formulated as a salt form, or a co-solvent may be added which is water-miscible and physiologically acceptable, e.g. dimethylsulfoxide and the like, or the compounds of formula (I) may be solubilized with a suitable carrier, e.g. a cyclodextrin (CD) or in particular a cyclodextrin derivative such as the cyclodextrin derivates described in U.S. Pat. No. 3,459,731, EP-A-149, 197 (Jul. 24, 1985), EP-A-197,571 (Oct. 15, 1986), U.S. Pat. No. 4,535,152 or WO 90/12035 (Oct. 18, 1990). Appropriate cyclodextrin derivatives are $\alpha$-,$\beta$-,$\gamma$-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy $C_{1-6}$alkyl, particularly hydroxyethyl, hydroxypropyl or hydroxybutyl; carboxy $C_{1-6}$alkyl, particularly carboxymethyl or carboxyethyl; $C_{1-6}$alkyl-carbonyl, particularly acetyl; $C_{1-6}$alkyloxycarbonyl $C_{1-6}$alkyl or carboxy $C_{1-6}$alkyl-oxy $C_{1-6}$alkyl, particularly carboxymethoxypropyl or carboxyethoxypropyl; $C_{1-6}$alkylcarbonyloxy $C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxy-methoxy)propyl-β-CD, and in particular 2-hydroxypropyl-β-CD. The term mixed ether denotes cyclodextrin derivatives wherein at least two cyclodextrin hydroxy groups are etherified with different groups such as, for example, hydroxypropyl and hydroxyethyl. The average molar substitution (M.S.) is used as a measure of the average number of moles of alkoxy units per mole of anhydroglucose. The M.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin hydroxyalkyl derivatives for use in the compositions according to the present invention the M.S. as determined by mass spectrometry is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR or IR preferably range from 0.3 to 1, in particular from 0.55 to 0.75. The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin derivatives for use in the compositions according to the present invention the D.S. as determined by MS is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR or IR preferably range from 0.3 to 1, in particular from 0.55 to 0.75. More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin is less than 5% of the total cyclodextrin content and in particular is less than 1.5%. Another particularly interesting cyclodextrin derivative is randomly methylated β-cyclodextrin. Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

It is especially advantageous to formulate the. aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Helicobacter related diseases it is evident that the present invention provides a method of treating warm-blooded animals, in particular humans, suffering from Helicobacter related diseases, said method comprising the systemic administration of a pharmaceutically effective amount of a compound of formula (I), a pharmaceutically acceptable addition salt thereof or a stereochemically isomeric form thereof, in admixture with a pharmaceutical carrier. In a further aspect of the invention, the subjects compounds are administered for use as a medicine.

In general it is contemplated that an effective daily amount would be from 0.05 mg/kg to 50 mg/kg body weight, preferably from 0.1 mg/kg to 30 mg/kg body weight and more preferably form 0.5 mg/kg to 10 mg/kg body weight. It is evident that said effective daily amount may be lowered or increased depending on the response of the treated subject and/or depending on the evaluation of the physician prescribing the compounds of the instant invention. The effective ranges mentioned hereinabove are therefore guidelines only and are not intended to limit the scope or use of the invention to any extent.

Optionally, other active compounds used for the eradication of Helicobacter can be administered in combination with the compounds of the present invention. The administration may occur separately (i.e. simultaneously, concurrently or consecutively) or the different drugs may be combined in one dosage form. Suitable compounds for a combination therapy are bismuth compounds, e.g. bismuth subcitrate, bismuth subsalicylate, and the like, antibiotics, e.g. ampicillin, amoxicillin, clarithromycin and the like, $H_2$-receptor antagonists, e.g. cimetidine, ranitidine and the like, and in particular, proton pump inhibitors, e.g. omeprazole, lansoprazole, pantoprazole and the like. For the compounds cited to be useful for a combination therapy with the compounds of formula (I) an effective daily amount would be from 0.05 mg/kg to 50 mg/kg body weight.

EXPERIMENTAL PART

Hereinafter, "DMSO" means dimethyl sulfoxide.

EXAMPLE 1 a) A mixture of (±)-ethyl 4-[5-[2-[1-(4-chlorobenzoyl)propyl]-2,3-dihydro-3-oxo-4H-1,2,4-triazol-4-yl]-2-pyridinyl]-1-piperazinecarboxylate (24 g) in hydrobromic acid, 48% solution in water (250 ml) was stirred and refluxed overnight. The solvent was evaporated and the residue was dissolved in $CH_2Cl_2$, neutralized with $NH_4OH/H_2O$ and extracted with $CH_2Cl_2$. The organic layer was washed with water, dried, filtered and evaporated. A sample (3.5 g) of the residue (total 18 g) was purified by column chromatography over silica gel (eluent: $CH_2Cl_2/(CH_3OH/NH_3)$ 99/1 ). The pure fractions were collected and evaporated. The residue was dissolved in 2-propanol and crystallized into the hydrochloric acid salt (1:1) in 2-propanol. The precipitate was filtered off, washed with 2-propanol and dried at 150° C. The product was dissolved in 2-propanol. Pyridine was added dropwise until all the product was dissolved and subsequently crystallized. The precipitate was filtered off and dried, yielding 1.7 g (±)-2-[1-(4-chlorobenzoyl)propyl]-2,4-dihydro-4-[6-( 1-piperazinyl)-3-pyridinyl]-3H-1,2,4-triazol- 3-one monohydrochloride (39.4%); mp. 209.8° C. (interm. 1). b) A mixture of benzenesulfonyl chloride (0.044 g) and intermediate 1(0.1 g) in CH₂Cl₂(10 ml) and N,N-diethylethanamine (1 ml) was stirred at room temperature overnight. The mixture was purified by HPLC over silica gel (eluent: CH₂Cl₂ 100 to CH₂Cl₂/CH₃OH 90/10 over a 20 minutes period and 120ml/min.). The desired fraction was collected and evaporated, yielding a solution of 0.119 g (85%) in DMSO (10.5 ml) of (±)-1-[5-[2-[1-(4-chlorobenzoyl)propyl]-2,3-dihydro-3-oxo-4H-1,2,4-triazol-4yl]-2-Pyridinyl]-4-(phenylsulfonyl)piperazine (comp. 1). In a similar manner were prepared:

Two drops of water were added and stirring was continued for 2 hours. CH₂Cl₂ was added until a total volume of 20 ml was reached. The mixture was centrifuged and filtered. MgSO₄ (spatula tip) was added and the mixture was separated by high-performance liquid chromatography over silica gel (eluent A: CH₂Cl₂; eluent B: CH₂Cl₂/CH₃OH 90/10; from 90% A and 10% B, over a 2-minute period (125 ml/min), to 90% A and 10% B; upgrading, over an 18-minute period (125 ml/min), to 100% B). The pure fractions were collected and the solvent was evaporated, yielding 0.054 g of (±)-(R*,R*)-1-[5-[2-[1-[(4-chlorophenyl)hydroxymethyl]propyl]-2,3-dihydro-3-oxo-4H-1,2,4-

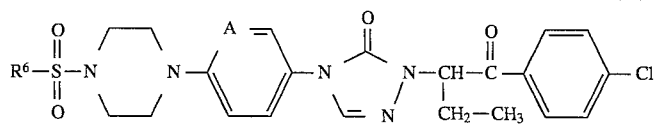

| Co. No. | R⁶ | A |
|---|---|---|
| 2 | 4-methylphenyl | N |
| 3 | 4-methoxyphenyl | N |
| 4 | 4-bromophenyl | N |
| 5 | 4-nitrophenyl | N |
| 6 | 4-(methylcarbonylamino)phenyl | N |
| 7 | methyl | N |
| 8 | 4-chlorophenyl | N |
| 9 | 4-fluorophenyl | N |
| 10 | phenyl | CH |
| 11 | 4-methylphenyl | CH |
| 12 | 4-methoxyphenyl | CH |
| 13 | 4-bromophenyl | CH |
| 14 | 4-nitrophenyl | CH |
| 15 | 4-(methylcarbonylamino)phenyl | CH |
| 16 | methyl | CH |
| 17 | 4-chlorophenyl | CH |
| 18 | 4-fluorophenyl | CH |

EXAMPLE 2

N,N-diethylethanamine (1 ml) and benzenesulfonyl chloride (excess; 0.06 g) were added to a solution of intermediate 1(0.1 g) in N,N-dimethylformamide (2 ml). The mixture was stirred for 6 hours at room temperature. K[OCH(CH₃)₂]₃BH 1M in tetrahydrofuran (1.5 ml) was added and the reaction mixture was stirred overnight at room temperature.

triazol-4-yl]-2-pyridinyl]-4-(phenylsulfonyl)piperazine (comp. 19). In a similar manner were prepared:

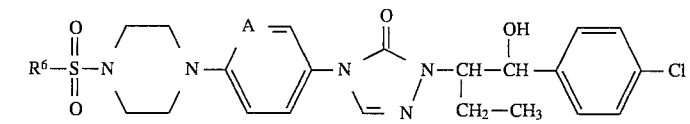

| Co. No. | R⁶ | A | physical data |
|---|---|---|---|
| 20 | 4-methylphenyl | N | (R*,R*) |
| 21 | 4-methoxyphenyl | N | (R*,R*) |
| 22 | 4-bromophenyl | N | (R*,R*) |
| 23 | 4-nitrophenyl | N | (R*,R*) |
| 24 | 4-(methylcarbonylamino)phenyl | N | (R*,R*) |
| 25 | methyl | N | (R*,R*) |
| 26 | 4-chlorophenyl | N | (R*,R*) |
| 27 | 4-fluorophenyl | N | (R*,R*) |
| 28 | phenyl | CH | (R*,R*) |
| 29 | 4-methylphenyl | CH | (R*,R*) |
| 30 | 4-methoxyphenyl | CH | (R*,R*) |
| 31 | 4-bromophenyl | CH | (R*,R*) |
| 32 | 4-(methylcarbonylamino)phenyl | CH | (R*,R*) |
| 33 | methyl | CH | (R*,R*) |

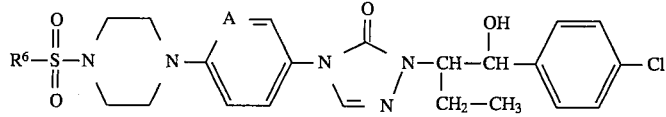

| Co. No. | R⁶ | A | physical data |
| --- | --- | --- | --- |
| 34 | 4-chlorophenyl | CH | (R*,R*) |
| 35 | 4-fluorophenyl | CH | (R*,R*) |

PHARMACOLOGICAL EXAMPLE

The anti-Helicobacter activity of the subject compounds was assessed by the following in vitro test procedure.

EXAMPLE 3

Activity of Test Compounds Verses Helicobacter

The activity of test compounds against *Helicobacter pylori* was determined against a standard set of 5 *H. pylori* strains obtained from clinical material. Minimal inhibitory concentrations (MICs) were determined by measuring the activity of *H. pylori* urease after treatment of growing cultures of the bacteria with the antimicrobial agents.

The test compounds were dissolved in DMSO at a concentration of $10^{-3}$M. A dilution to $10^{-4}$M in DMSO was also prepared. 10 μl. volumes of these solutions were pipetted in the wells of Repli-Dishes (®Sterilin). Wells containing DMSO alone were included as controls in each Repli-Dish. Ampicillin ((+)-6-[(2-amino-2-phenylacetyl)amino]-3,3-dimethyl-7-oxo-4-thia-1-azabicyclo[3.2.0]heptane-2-carboxylic acid. trihydrate) and metronidazole (2-methyl-5-nitro-1H-imidazol-1-ethanol) were included as reference compounds in each batch of tests. (These compounds were tested at final concentrations of $10^{-5}$, $10^{-6}$, $10^{-7}$ and $10^{-8}$M). Test plates were stored at 4° C. until used. The five isolates of *H. pylori* were maintained by subculture on 10% blood agar every 2 or 3 days. The bacteria were grown at 37° C. under an atmosphere containing 5% oxygen, 10% $CO_2$ and 85% nitrogen. Suspensions of *Helicobacter pylori* for inoculum were prepared in Brain-heart infusion broth and adjusted to an absorbance of 1.5±0.3 at 530 nM.

Freshly prepared 10% blood agar held at 45° C. was added in 1 ml volumes to the wells of the test plates, thus diluting the test compounds to $10^{-5}$ and $10^{-6}$M. The medium was allowed to cool, then 10 μl volumes of bacterial suspension were pipetted on the agar surface. The plates were incubated for 48 hours at 37° C. under the microaerophilic atmosphere described above. To facilitate reading of the plates and to ensure that any growth on the media was truly *H. pylori*, advantage was taken of the highly potent urea activity unique to this species. After the 48 hours of incubation, 1 ml volumes of urease broth were gently added to each Repli-Dish well and the plates were incubated at 37° C. for 2 hours. 100 μl samples of fluid from each well were then pipetted into the wells of 96-place microdilution plates. A purple colour was interpreted as growth, yellow-orange as no growth of *H. pylori*. By this means a clear end-point was obtained, from which the inhibitory effects could be determined. All compounds that showed activity at either of the two concentrations tested were retested with further dilutions included to establish the MIC and with a broader spectrum of bacterial species as target organisms. Thus far, the MIC value for compound 25 was found to be equal or below 10 μM.

COMPOSITION EXAMPLES

"Active ingredient" (A.I.) as used throughout these examples relates to a compound of formula (I), a pharmaceutically acceptable acid addition salt or a stereochemically isomeric form thereof.

EXAMPLE 4

Oral Drops

500 Grams of the A.I. was dissolved in 0.5 l of 2-hydroxypropanoic acid and 1.5 l of the polyethylene glycol at 60°–80° C. After cooling to 30°–40° C. there were added 35l l of polyethylene glycol and the mixture was stirred well. Then a solution of 1750 grams of sodium saccharin in 2.5 l of purified water was added. Upon stirring were added 2.5 l of cocoa flavor and polyethylene glycol q.s. to a volume of 50 l, providing an oral drop solution comprising 10 mg/ml of A.I.. The resulting solution was filled into suitable containers.

EXAMPLE 5

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 6

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in 200 ml of water. The wet powder mixture was sieved, dried and sieved again. 100 Grams microcrystalline cellulose and 15 grams hydrogenated vegetable oil were added. The whole was mixed well and compressed into tablets, giving 10.000 tablets, each containing 10 mg of the active ingredient.

Coating

To a solution of 10 grams methyl cellulose in 75 ml of denaturated ethanol was added a solution of 5 grams of ethyl cellulose in 150 ml of $CH_2Cl_2$. Then there were added 75 ml of $CH_2Cl_2$ and 2.5 ml 1,2,3-propanetriol. 10 Grams of polyethylene glycol was molten and dissolved in 75 ml of $CH_2Cl_2$. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 7

Suppositories

3 Grams A.I. was dissolved in a solution of 3 grams 2,3-dihydroxybutanedioic acid in 25 ml polyethylene glycol 400.12 Grams surfactant and triglycerides q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

We claim:

1. A compound having the formula

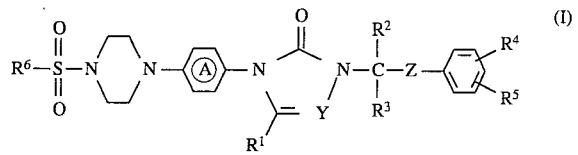
(I)

a pharmaceutically acceptable addition salt or a stereochemically isomeric form thereof, wherein Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is $C_{1-4}$alkyl; or phenyl optionally substituted with halo, $C_{1-4}$alkylcarbonylamino, $C_{1-4}$alkyloxy, $C_{1-4}$alkyl or nitro;

Z is C=O or CHOH; and

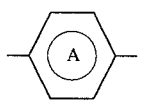

is a radical of formula

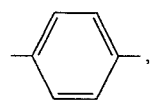
(a-1)

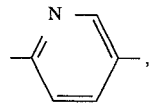
(a-2)

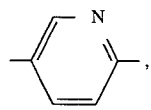
(a-3)

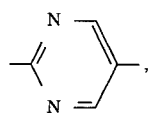
(a-4)

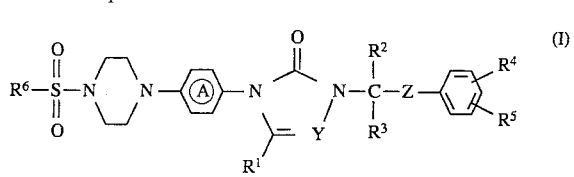
(a-5)

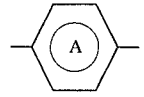
(a-6)

or

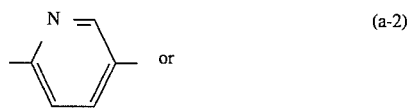
(a-7)

2. A compound according to claim 1 wherein $R^1$, $R^3$ and $R^5$ are hydrogen;

$R^2$ is $C_{1-4}$alkyl;

$R^4$ is halo; and

Y is N.

3. A compound according to claim 2 wherein $R^2$ is ethyl;

$R^6$ is $C_{1-4}$alkyl; and

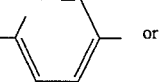

is a radical of formula (a–1) or (a–2).

4. A compound of the formula:

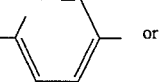
(I)

a pharmaceutically acceptable addition salt or a stereochemically isomeric form thereof, wherein:

Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy of difluoromethyloxy;

$R^6$ is $C_{1-4}$alkyl; or phenyl optionally substituted with halo, $C_{1-4}$alkylcarbonylamino, $C_{1-4}$alkyloxy, $C_{1-4}$alkyl or nitro;

Z is C=O or CHOH; and

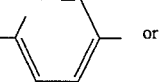

is a radical of the formula:

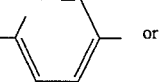
(a-2)

or

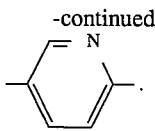

5. A compound according to claim 4 wherein said compound is 1-[5-[2-[1-[(4-chlorophenyl)hydroxymethyl]propyl]-2,3-dihydro-3-oxo-4H-1,2,4-triazol-4-yl]-2-pyridinyl]-4-(methylsulfonyl)piperazine, a pharmaceutically acceptable addition salt or a stereochemically isomeric form thereof.

6. A compound according to claim 10 wherein:

$R^1$, $R^3$ and $R^5$ are hydrogen;

$R^2$ is $C_{1-4}$alkyl;

$R^4$ is halo; and

Y is N.

7. A compound according to claim 6 wherein $R^2$ is ethyl and $R^6$ is $C_{1-4}$ alkyl.

8. A method of treating Helicobacter infection which comprises administering to patients infected with Helicobacter a therapeutically effective amount of a compound as defined in claim 4.

9. A method of treating Helicobacter infection which comprises administering to patinets infected with Helicobacter a therapeutically effective amount of a compound as defined in claim 6.

10. A method of treating Helicobacter infection which comprises administering to patients infected with Helicobacter a therapeutically effective amount of a compound as defined in claim 7.

11. A method of treating Helicobacter infection which comprises administering to patients infected with Helicobacter a therapeutically effective amount of a compound as defined in claim 4.

12. A composition comprising a therapeutically effective amount of a compound as defined in claim 4 and a pharmaceutically effective carrier.

13. A composition comprising a therapeutically effective amount of a compound as defined in claim 6 and a pharmaceutically effective carrier.

14. A composition comprising a therapeutically effective amount of a compound as defined in claim 7 and a pharmaceutically effective carrier.

15. A composition comprising a therapeutically effective amount of a compound as defined in claim 4 and a pharmaceutically effective carrier.

16. A pharmaceutical composition comprising a therapeutically effective amount of a compound as claimed in any of claims 1 to 3 and a pharmaceutically acceptable carrier.

* * * * *